US011007046B2

(12) United States Patent
Yachia et al.

(10) Patent No.: US 11,007,046 B2
(45) Date of Patent: May 18, 2021

(54) STENT AND METHOD OF USE

(71) Applicant: INNOVENTIONS LTD., Or Akiva (IL)

(72) Inventors: Daniel Yachia, Herzlia (IL); Valentin Ponomarenko, Haifa (IL)

(73) Assignee: INNOVENTIONS LTD., Or Akiva (IL)

( * ) Notice: Subject to any disclaimer, the term of this patent is extended or adjusted under 35 U.S.C. 154(b) by 299 days.

(21) Appl. No.: 15/574,993

(22) PCT Filed: May 22, 2016

(86) PCT No.: PCT/IL2016/050536
§ 371 (c)(1),
(2) Date: Nov. 17, 2017

(87) PCT Pub. No.: WO2016/185482
PCT Pub. Date: Nov. 24, 2016

(65) Prior Publication Data
US 2018/0140414 A1  May 24, 2018

Related U.S. Application Data

(60) Provisional application No. 62/164,049, filed on May 20, 2015.

(51) Int. Cl.
*A61F 2/04* (2013.01)
*A61M 27/00* (2006.01)
*A61B 17/00* (2006.01)

(52) U.S. Cl.
CPC ........... *A61F 2/042* (2013.01); *A61M 27/008* (2013.01); *A61B 2017/00871* (2013.01); *A61F 2002/048* (2013.01)

(58) Field of Classification Search
CPC ..................... A61F 2002/047; A61F 2002/048
See application file for complete search history.

(56) References Cited

U.S. PATENT DOCUMENTS

| 5,019,102 A | * | 5/1991 | Hoene | A61M 25/0069 604/264 |
| 5,531,718 A | * | 7/1996 | Sachse | A61F 2/94 604/530 |
| 2001/0021835 A1 | | 9/2001 | Mitchell et al. | |
| 2008/0086214 A1 | | 4/2008 | Hardin et al. | |
| 2011/0320008 A1 | | 12/2011 | Teague et al. | |
| 2012/0053700 A1 | | 3/2012 | Rickner | |

FOREIGN PATENT DOCUMENTS

WO   WO-2013185128 A1 * 12/2013

* cited by examiner

*Primary Examiner* — Megan Y Wolf
(74) *Attorney, Agent, or Firm* — Robert G. Lev

(57) ABSTRACT

A urinary stent includes ends for deployment in the kidney and bladder, respectively, that are non-coplanar. The bladder end of the stent includes a luminary groove, covered by a sleeve of materials softer than the remainder of the stent, allowing urine at sufficient pressures to pass out from the stent, between the stent and the sleeve. The bladder end of the stent adapts its shape according to respiratory changes in the length of the stent. This shape change also prevents or reduces stent related pain.

36 Claims, 14 Drawing Sheets

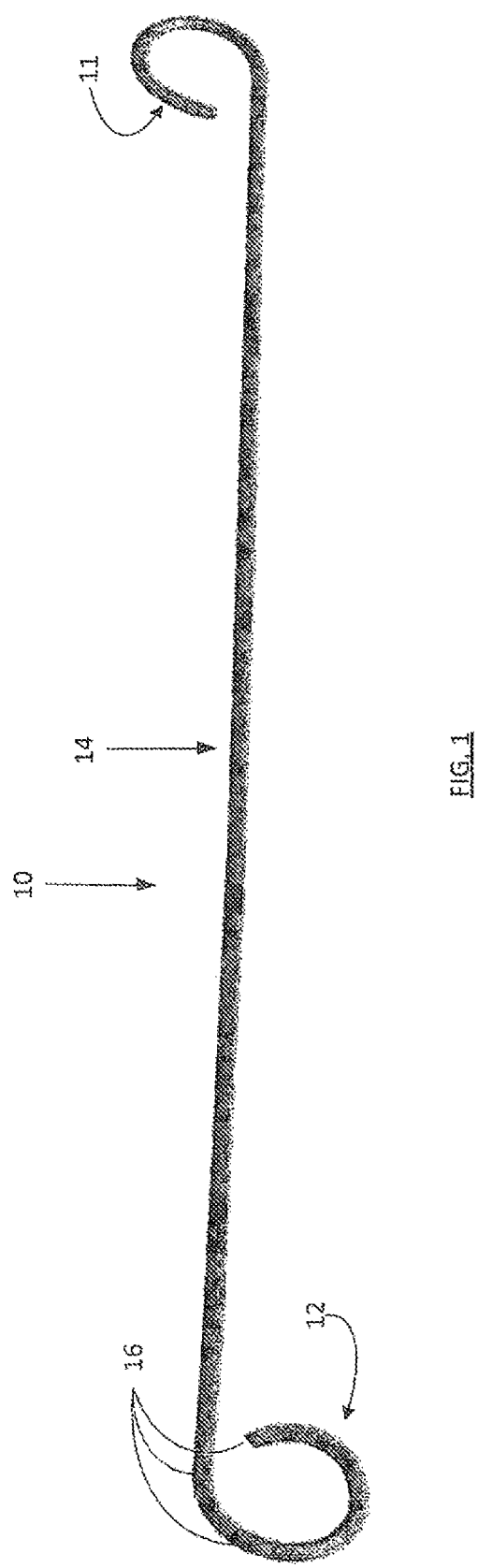

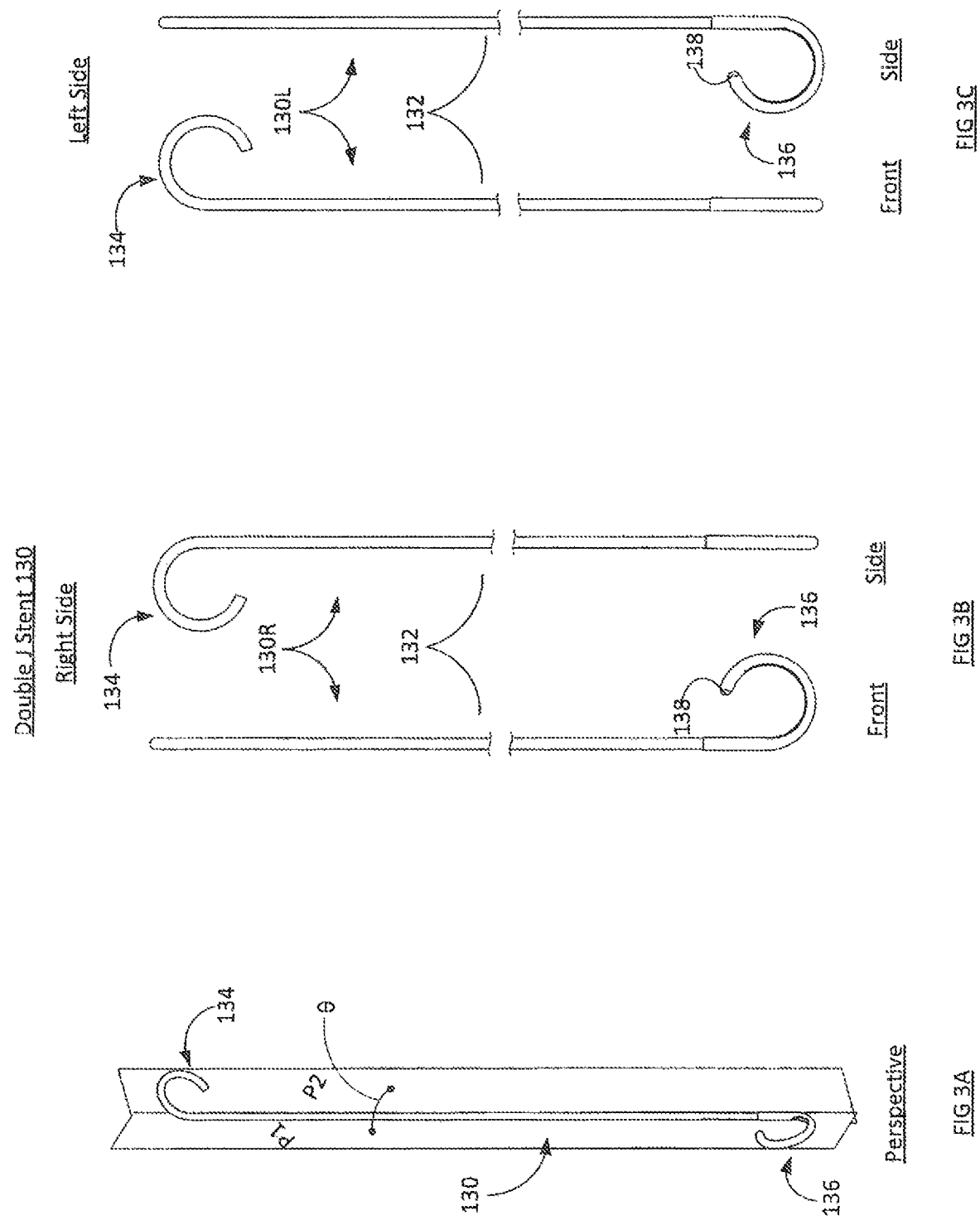

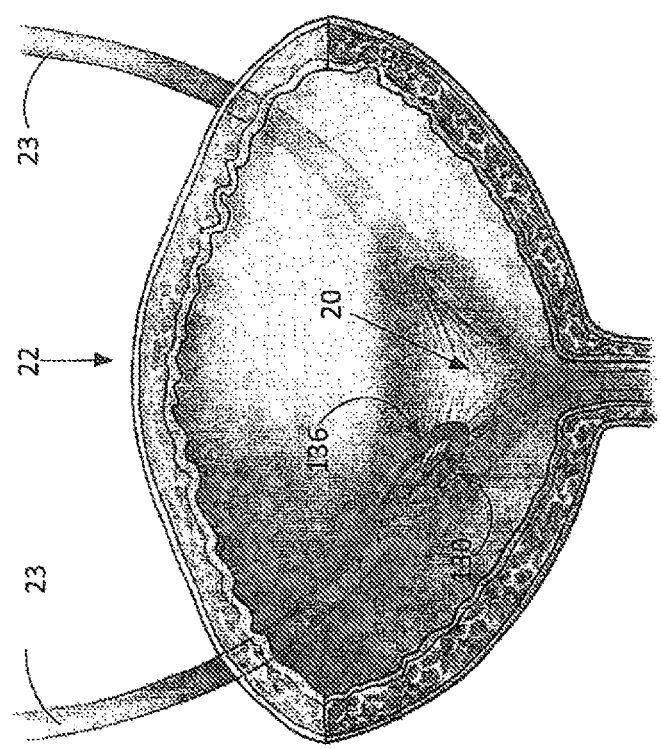

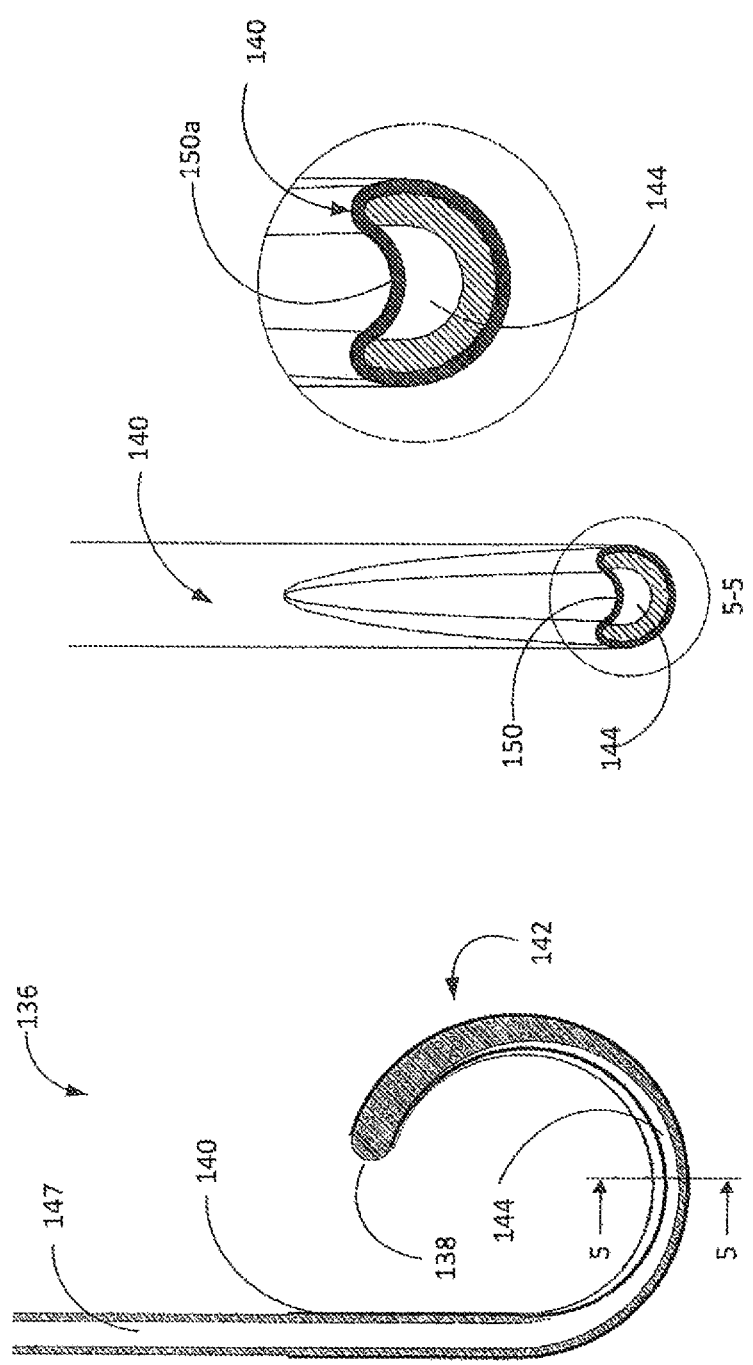

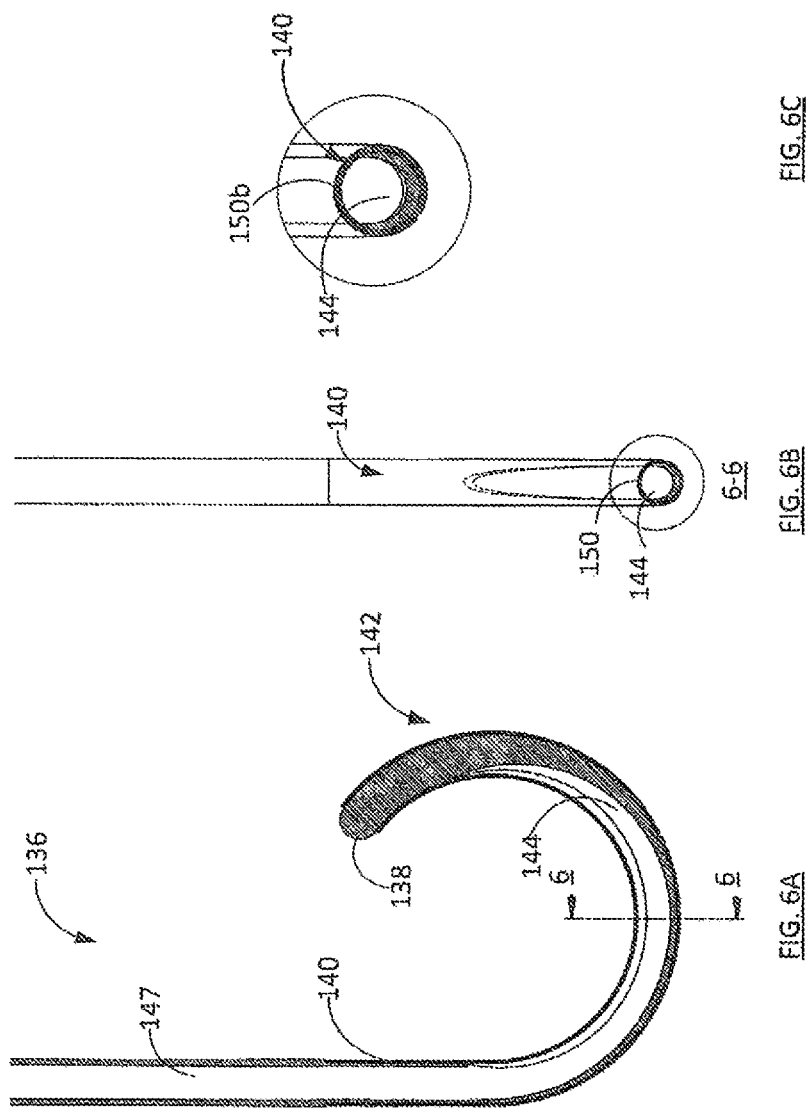

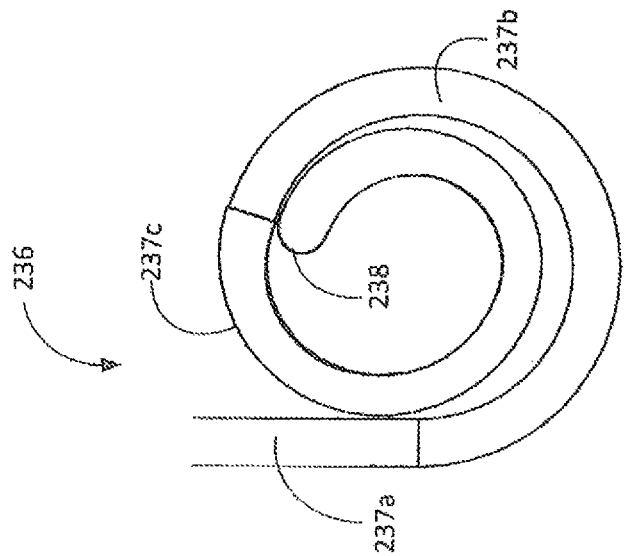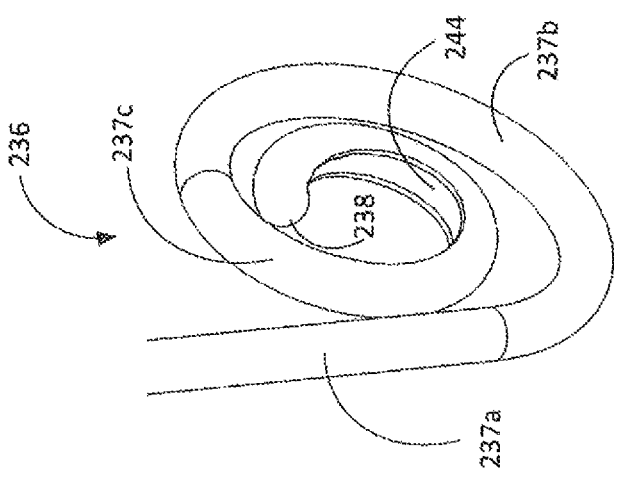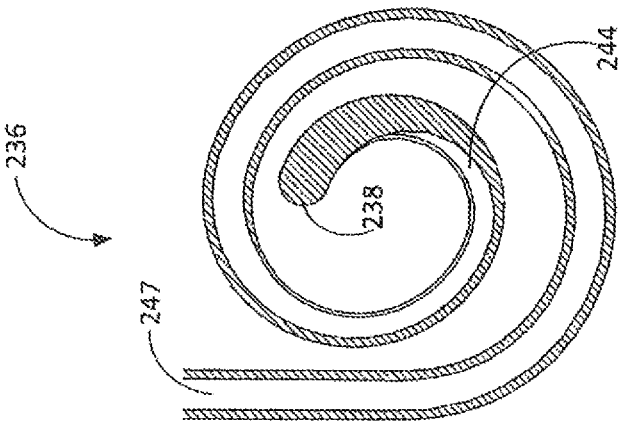

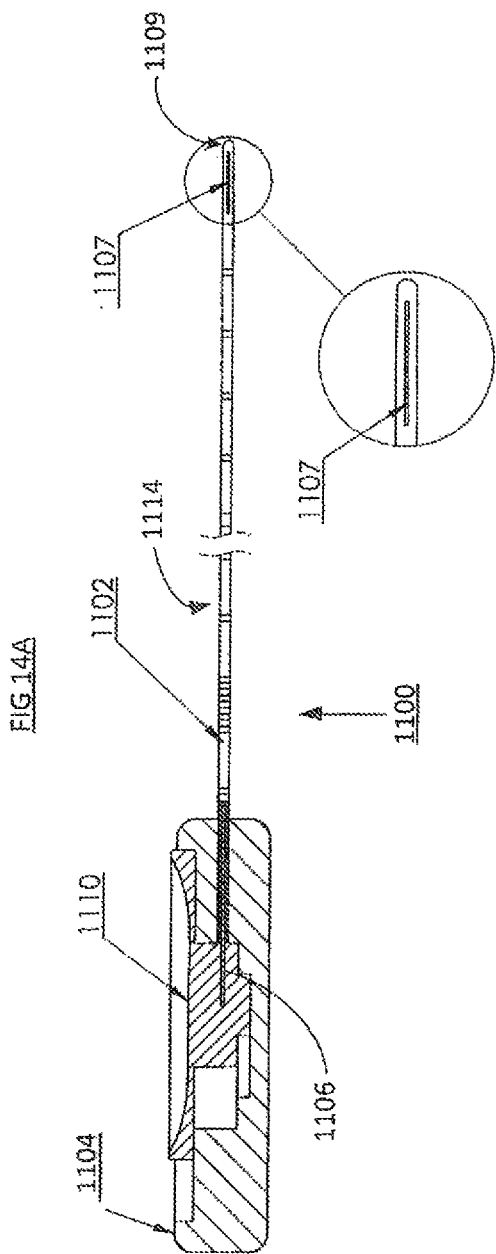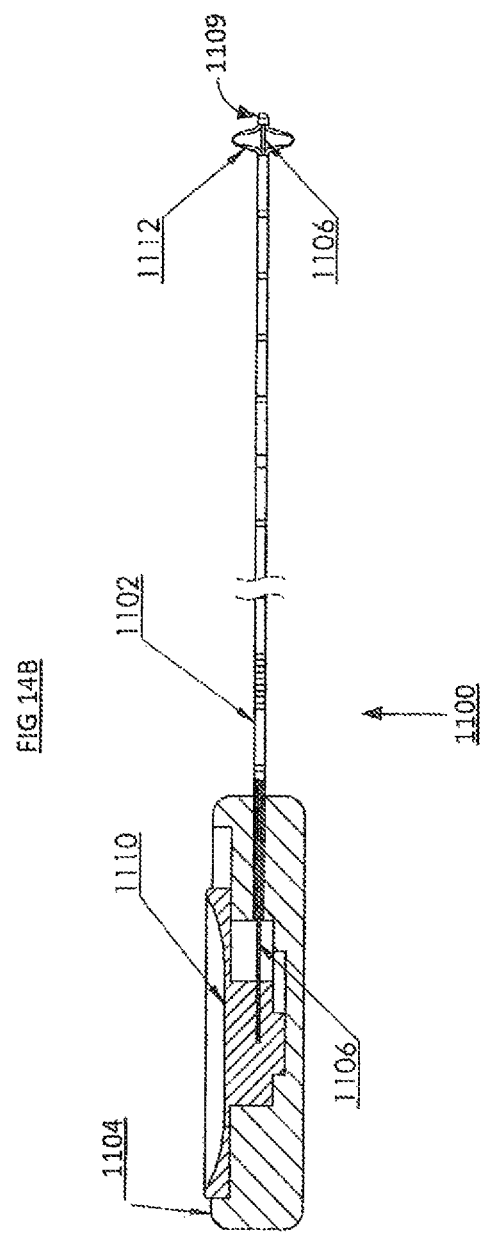

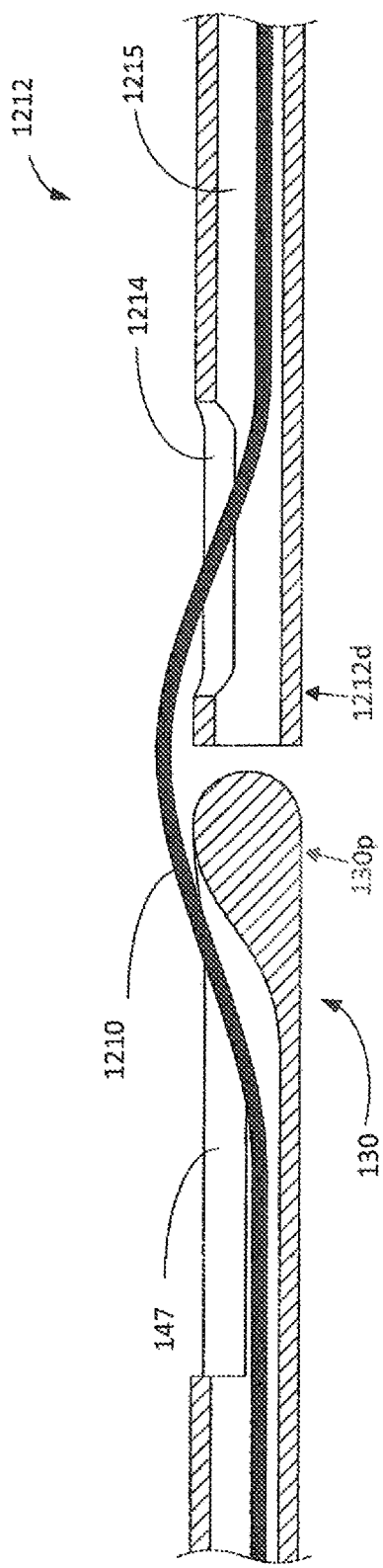

STENT AND METHOD OF USE

CROSS REFERENCE TO RELATED APPLICATIONS

This application is related to and claims priority from commonly owned U.S. Provisional Patent Application Ser. No. 62/164,049, entitled: Stent and Method of Use, filed on May 20, 2015, the disclosure of which is incorporated by reference herein in its entirety.

FIELD AND BACKGROUND OF THE INVENTION

The present invention, in some embodiments thereof, relates to urinary stents and, more particularly, but not exclusively, to stents used in, urologic or other applications.

Ureteral stents, in particular stents known as Double-J stents and Pigtail stents, due to their J-shaped and pigtail ends, respectively, have been in common usage, to relieve ureteral obstructions, typically between the kidney and the bladder, for the past 40 plus years. Little has changed with these stents, since their development by Dr. Roy P. Finney in the 1970's.

As shown in FIG. 1, a Double-J stent 10, exemplary of conventional Double-J stents and pigtail stents, has kidney 11 and bladder 12 ends, both of which are coiled. A body 14 which extends between the ends 11, 12, these ends 11, 12 are oriented coplanar (along the body 14) with respect to each other.

These stents 10 are commonly used as drains, to allow fluid, including urine, to drain from the kidney into the bladder, through openings 16, after the patient had either a stone blocking the ureter (tube leading between kidney and bladder), a stricture or a tumor compressing or infiltrating the ureter and blocking it or had a diagnostic or therapeutic procedure where the surgeon passed a ureteroscope from the bladder into the ureter to break a stone or dilate a stricture. Such manipulations may cause a transient edematous blockage of the ureter.

Should a Double-J stent or pigtail stent not have been left in place, there would be a strong likelihood of the patient suffering symptoms of renal colic caused by the ureteric peristaltic contractions trying to drain the urine, and severe loin pain, and that blockage can cause back pressure on the kidney. This back pressure, if left untreated, can eventually lead to damage of the kidney.

More than 1.5 Million Double-J and pigtail stents are used a year worldwide. The "J-shaped" curvature or the pig-tail at both ends provide anchoring, by creating a self-retaining capability of the stent to the renal pelvis and the bladder to prevent its upward or downward, migration, even during ureteral peristalsis and respiration, where the kidneys move up and down.

Numerous attempts have been made to make these Double-J and pigtail ureteral stents more comfortable for the patients, in particular, to reduce trigonal irritation. Such improvements intended to reduce trigonal irritation have included making the entire bladder end of the stent from the same material like their bodies, but of a lower durometer, to make them softer, or from softer material. Other attempted improvements have involved or changing the bladder end anchoring segment to loops, or coating the stents with hydrophilic materials or adding a flat balloon shaped valve at its bladder end to prevent urine reflux from the bladder to the kidney. However, patient comfort improved minimally at best.

Symptoms of reactions to these Double-J and pigtail stents occur in approximately 80% of all patients. The most prevalent symptoms are: 1) frequency to urinate (up to 60%), 2) urgency/urge incontinence (up to 60%), and, 3) flank pain (up to 35%). These symptoms can appear either alone or in various combinations.

Frequency and urgency are caused by the stent by the mechanical irritation of the bladder trigone area 20, as shown in FIG. 2A. The bladder trigone 20 is an anatomical, entity, triangular in shape, formed in the bladder 22 by the two ureteral orifices 23a and the bladder neck 24. The bladder 22 connects to the urethra at an opening called the bladder neck 24, through which the ureters 23 are reachable in endoscopic interventions.

Turning also to FIG. 2B, this mechanical irritation is, for example, induced by the curl or coil at the bladder end 12 of the conventional Double-J stent 10, as a result of the coils, of the respective ends (kidney 11 and bladder 12) being coplanar.

Normally when the trigone stretches to a certain degree it induces the signals of bladder filling that reach the brain. This feeling can also happen when, the bladder is not full but there is a foreign-body like a ureteral stent or a bladder stone coming in contact with the trigonal area. This mechanical irritation causes the urgency and frequency in urinating even when the bladder is not full. It is less felt during the nights when the awareness of this irritation is less during sleep.

Flank pain results from urine refluxing through the stent, from the bladder towards the kidney. Increase of the intra-renal pressure when the bladder pressure increases, during its filling and voiding, induces the pain. This flank pain is caused by the inherent design flaws common in contemporary Double-J and pigtail stents.

Contemporary Double-J and pigtail stents have a two-dimensional design, in which the pelvic and bladder ends are on the same plane. Because of this design, the bladder end 12 of the stent 10 is almost always in contact with the bladder trigone 20 causing the aforementioned reactions and conditions.

Additionally, during respiration, the up and down movement of the kidney moves also the bladder end 12 of the stent 10 into the bladder 22 and then back. This movement creates a continuously repeating friction with the trigone. This movement of the stent 10 into the bladder 22 may be up to four centimeters.

SUMMARY OF THE INVENTION

The present invention is directed to urinary stents, including Double-J stents and pigtail stents. A Double-J stent in this application is a stent whose ends are curled or coiled, so as to be in a J-shape. A pigtail stent has ends that are curled or coiled, beyond a J-configuration, with at least one overlap. Throughout this document, the disclosure, including features, properties and the like, for the Double-J stents applies to the pigtail stents, and vice versa, except where specifically indicated.

Embodiments of the present invention include urinary stents. These urinary stents include ends for deployment in the kidney and bladder, respectively, that are non-coplanar. The bladder end of the stent includes a luminary groove, covered by a sleeve of materials softer than the remainder of the stent, allowing urine at sufficient pressures to pass out from the stent, between the stent and the sleeve. The bladder end of the stent adapts its shape according to respiratory changes in the length of the stent. This shape change also prevents or reduces stent related pain.

According to some embodiments of the present invention, a urinary stent, for example, in a double-J configuration, includes ends for deployment in the kidney and bladder, respectively, that are non-coplanar. The bladder end of the stent includes a luminary groove covered by a sleeve made of a flexible and radially elastic material softer than the materials of the remainder of the stent, allowing urine at sufficient pressures to pass out from the stent, between the stent and the sleeve, pressure of the urine pushing or expanding a part of the tip of the sleeve to elevate it and allow passage to urine. The sleeve is pre-shaped to collapse inward or it may collapse inward (toward the groove) to occlude the lumen when the pressure in the bladder increases, to prevent urine reflux from the bladder through the stent toward the kidney.

In other embodiments, there is provided a Double-J stent which reduces frictional contact with the trigonal area, by the bladder end being oriented approximately 90 degrees with respect to the renal end, to prevent the continuous contact between the bladder end of the stent with the trigone resulting in with the feeling of urine frequency and urgency, even when the bladder is not full.

The present invention, in some embodiments thereof, relates to a urinary stent and, more particularly, but not exclusively, to a Double-J and pigtail stents for use in the ureter.

The present invention, in some embodiments, is directed to a novel design for improving Double-J and pigtail stents and preventing, or significantly reducing, stent induced symptoms.

In some embodiments of the present invention, the axis of the bladder end segment of the Double-J stents and pigtail stents are positioned along different planes, the planes oriented approximately perpendicular to each other. Accordingly, the ends of the stents, either J-shaped, or coiled are oriented approximately perpendicular to each other. This angling allows for the bladder end of each stent, to have minimal frictional contact with the trigone region of the bladder, inhibiting irritative symptoms.

Other embodiments of the present invention accommodate inspiration and expiration related up and down movements of the kidneys during respiration and compensate for the up to four centimeter length of the stent entering into the bladder and retracting back, for eliminating it the pain and irritation associated with these movements.

Still other embodiments of the present invention detail Double-J and pig tail stents with the bladder end luminary groove covered by a sleeve of a flexible and radially elastic material softer than the materials of the rest of the stent. This allows urine to exit between the sleeve and the bladder end, and, also, the sleeve to collapse, inward, when no urine flows from the kidney to the bladder or when the pressure in the bladder increases, or it is pre-shaped to collapse toward the groove to prevent urine reflux through the stent toward the kidney, which causes flank pain.

Some embodiments of the present invention allow the bladder end of the Double-J and pigtail stents to change geometry during while deployed in the body, in response to movement of the kidneys with respect to the bladder during respiration.

Embodiments of the present invention are directed to a stent. The stent comprises: a body including oppositely disposed first and second curled ends, the first curled end extending along a first plane and the second curled end extending along a second plane. The first and second planes are at different orientations with respect to each other.

Optionally, the different orientations of the first and second planes with respect to each other include angles ranging from approximately 60 degrees to approximately 120 degrees.

Optionally, the different orientations of the first and second planes with respect to each other include a perpendicular orientation.

Optionally, the first curled end and the second curled end are moveable between a curled position and a partially uncurled position to accommodate the respiration of the user.

Optionally, the second curled end is configured for placement at least partially in the bladder.

Optionally, the body is tubular and includes: an outer surface; an interior (inner) lumen; the second curled end of the body including a groove extending through the body into the lumen, from the outer surface of the body: and, a sleeve extending at least partially along the groove over the body.

Optionally, the sleeve extends beyond the ends of the groove.

Optionally, the sleeve is of a material of a softer durometer than the body of the stent.

Optionally, the sleeve is of a material that when subject to a predetermined pressure of liquid, e.g., urine, in the second curled end, the sleeve expands to allow liquid egress from the second curled end.

Another embodiment of the present invention is directed to a stent. The stent comprises a body and a sleeve extending over and along a portion of the body. The body includes: an inner (interior) lumen; oppositely disposed first and second curled ends, and, an outer surface; and, the second curled end including a groove extending through the body into the lumen from the outer surface of the body. The sleeve extends at least partially along the groove.

Optionally, the sleeve extends beyond the ends of the groove.

Optionally, the sleeve is of a material of a softer durometer than the body of the stent.

Optionally, the sleeve is of a material that when subject to a predetermined pressure of liquid, e.g., urine, in the second curled end, the sleeve expands to allow liquid egress from the second curled end.

Optionally, the first curled end extends along a first plane and the second curled end extends along a second plane, the first and second planes at different orientations with respect to each other.

Optionally, the different orientations of the first and second planes with respect to each other include angles ranging from approximately 60 degrees to approximately 120 degrees.

Optionally, the different orientations of the first and second planes with respect to each other include a perpendicular orientation.

Optionally, the first curled end and the second curled end are moveable between a curled position and a partially uncurled position to accommodate the respiration of the user.

Optionally, the second curled end is configured for placement at least partially in the bladder.

Optionally, the body is tubular.

Other embodiments of the present invention are directed to a drainage device. The drainage device comprises: a body including an inner lumen, the body including oppositely disposed first and second curled ends, the first curled end extending along a first plane and the second curled end extending along a second plane, and, the first and second planes at different orientations with respect to each other.

Optionally, the different orientations of the first and second planes with respect to each other include angles ranging from approximately 60 degrees to approximately 120 degrees.

Optionally, the different orientations of the first and second planes with respect to each other include a perpendicular orientation.

Optionally, the body is tubular and includes a lumen extending therethrough, and the second end includes a groove extending through the body to the lumen from the outer surface the body, the groove extending along the outer surface of the body; and, a sleeve extending at least partially along the groove over the body.

Optionally, the sleeve extends beyond the ends of the groove.

Optionally, the sleeve is of a material of a softer durometer than the body.

Optionally, the sleeve is of a material that when subject to a predetermined pressure of liquid in the second curled end, the sleeve expands to allow liquid egress from the second curled end.

Optionally, the body defines a stent.

Optionally, the stent is, one of a urinary stent, biliary stent, and a pancreatic stent.

Optionally, the device is a urinary stent and the first curled end and the second curled end are moveable between a curled position and a partially uncurled position to accommodate, the respiration of the user.

Optionally, the second curled end is configured for placement at least partially in the bladder.

Another embodiment is directed to a drainage device. The drainage device comprises a tubular body and a sleeve, which extends over and along a portion of the tubular body. The tubular body includes: an inner (interior) lumen, oppositely disposed first and second curled ends, and, an outer surface. The second curled end includes a groove extending through the tubular body into the lumen from the outer surface of the tubular body. The sleeve extends at least partially along the groove.

Optionally, the sleeve extends beyond the ends of the groove.

Optionally, the sleeve is of a material of a softer durometer than the tubular body.

Optionally, the sleeve is of a material that when subjected to a predetermined pressure of liquid in the second curled end, the sleeve expands to allow liquid egress from the second curled end.

Optionally, the first curled end extends along a first plane and the second curled end extends along a second plane, the first and second planes at different orientations with respect to each other.

Optionally, the different orientations of the first and second planes with respect to each other include angles ranging from approximately 60 degrees to approximately 120 degrees.

Optionally, the different orientations of the first and second planes with respect to each other include a perpendicular orientation.

Optionally, the tubular body defines a stent.

Optionally, the stent is selected from one of urinary stents, biliary stents, and pancreatic stents.

Optionally, the device is a urinary stent and the first curled end and the second curled end are moveable between a curled position and a partially uncurled position to accommodate the respiration of the user.

Optionally, the second curled end is configured for placement at least partially in the bladder.

Embodiments of the invention are directed to methods for facilitating urine drainage. These methods comprise: providing a stent including oppositely disposed first and second curled ends, each of the first and second cads including openings in communication with a hollow interior of the stent for fluid flow therethrough, the first curled end extending along a first plane and the second curled end extending along a second plane, the first and second planes at different orientations with respect to each other; and, deploying the stent via the ureter, wherein the first end extends at least to the kidney and the second end extends at least into the bladder, such that the first end along the first plane is disposed at an angle from the second end along the second plane.

Optionally, the angle is approximately 30 to 150 degrees.

Optionally, the angle is approximately 90 degrees.

Optionally, the providing the stent includes measuring the ureter from the kidney to the bladder, and selecting the stent according to the measured length of the ureter.

Optionally, the deploying includes moving the stent along a guide wire.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings, where like reference numerals or characters represent corresponding or like elements. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a perspective view of a conventional Double-J stent;

FIG. 3A is a perspective view of a Double-J stent in accordance with an embodiment of the present invention;

FIG. 3B are front and side views of right side stent in accordance with the embodiment of FIG. 3A;

FIG. 3C are front and side views of left side stent in accordance with the embodiment of FIG. 3A;

FIG. 4 is a diagram of the bladder showing the Double-J stent of FIG. 3B deployed in the bladder and the bladder end in substantially out of frictional contact with the trigone of the bladder;

FIG. 5A is a longitudinal sectional view of the bladder end of another embodiment of the Double-J stent of the present invention with its pre-formed sleeve;

FIG. 5B is a front view cross section of the bladder end of the Double-J stent and pre-formed sleeve of FIG. 5A;

FIG. 5C is a detailed view of the bladder end of the stent of FIG. 5A from circle 5-5 of FIG. 5B;

FIG. 6A is a cross sectional view of the bladder end of the embodiment of the Double-J stent and cylindrical sleeve of the FIGS. 5A-5C in a second position;

FIG. 6B is a front view of the bladder end of the Double-J stent and the cylindrical sleeve of FIG. 6A;

FIG. 6C is a detailed view of the bladder end of the stent of FIG. 6A from circle 6-6 of FIG. 6B;

FIG. 10A is a longitudinal sectional view of the bladder end of the Pigtail Stent of FIG. 9A, with the sleeve not attached;

FIG. 10B is a perspective view of the bladder end of the Pigtail Stent of FIG. 9A, with the sleeve not attached;

FIG. 10C is a side view of the bladder end of the Pigtail Stent of FIG. 9A, with the sleeve not attached;

FIG. 14A is a perspective view of a measuring device in an unopened position;

FIG. 14B is a perspective view of a measuring device in a opened position; and,

FIG. 15 is a cross sectional view of a pusher member for deploying the stents of the embodiments of the present invention.

DETAILED DESCRIPTION

Figure 2B:
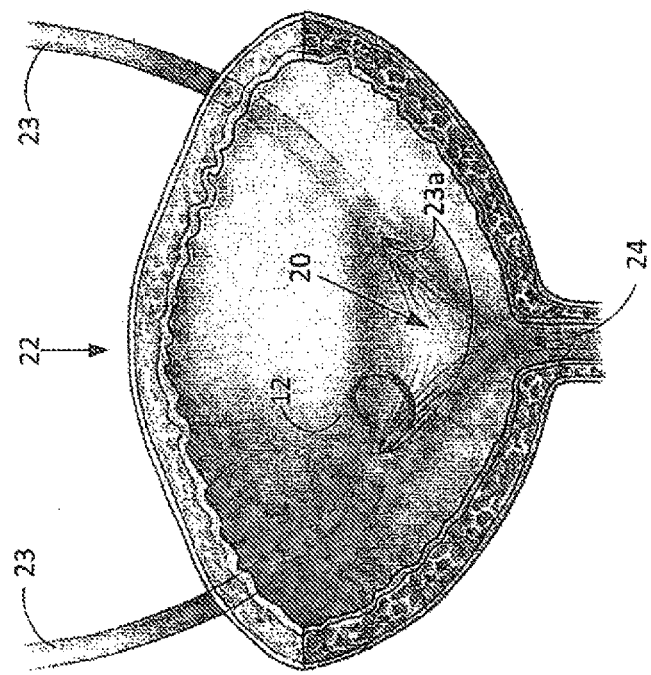
FIG. 2B is a diagram of the bladder showing a conventional Double-J stent of FIG. 1 deployed in the bladder and its bladder end in frictional contact with the trigone of the bladder.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Attention is directed to FIGS. 3A-3C. FIG. 3A shows a perspective view of an apparatus or drainage device, for example, a Double-J stent 130 in accordance with embodiments of the present invention. The stent 130 may be either a right side stein (or right stent) 130R, as shown in FIG. 3B, for placement in the right ureter, or a left side stent (or left stent 130L), as shown in FIG. 3C for placement in the left ureter. Here, "left" and "right" area defined according to the corresponding "left" and "right" hands of the mammalian subject in whom the stents 130 are being deployed.

As shown in the stent 130, applicable to, and representative of, both the right 130R and left 130L stents, the stent 130 includes a body 132, which is tubular, for example, typically rounded or circular in cross section (alternately, the body 132 may be square, triangular or any polygonal shape or undulating in cross section). The interior or inside of the body 132 is, for example, and hollow, single or multi-lumen. The body 132 includes a first or kidney end 134, and an opposite second or bladder end 136. The ends 134, 136 are curled or coiled (the terms "curled" and "coiled" used interchangeably herein), for example, into a J-shape, and are designed for moving between the curled or coiled and partially uncurled or partially uncoiled positions to accommodate respiration, where the kidneys and bladder may move apart, by approximately 4 centimeters. The ends 134, 136 are oriented with respect to each other at an angle θ, between plane P1, along which the bladder end 136 is coplanar, and plane P2, along which the kidney end 134 is coplanar. This angle θ, between the planes P1 and P2, is, for example, approximately 90 degrees, whereby the ends 134 (P2) and 136 (P1) are oriented bi-planar and the planes P1 and P2 are approximately perpendicular to each other, with angles θ of, for example, approximately 30 degrees to approximately 150 degrees, also permissible. This angling of the ends 134, 136 allows for the bladder end 136 of the stents 130R, 130L to have minimal, if any, frictional contact with the trigone 20 of the bladder 22. For example, as shown in FIG. 4, as the bladder end 136 of the right side stent 130R is oriented approximately 90 degrees with respect to the trigone 20 and not having a contact with the trigonal surface 20.

Turning also to FIGS. 5A-5C, 6A-6C, 7 and 8, the stent 130 is representative of stents 130R and 130L, as detailed above and shown in FIGS. 3B and 3C, respectively. Additionally, the construction detailed for the stent 130 is identical for both the right side 130R and left side 130L stents, detailed above and shown in FIGS. 3B and 3C, respectively.

FIGS. 5A-5C and 6A-6C show the bladder end 136 in detail. The bladder end 136, terminates in a tip 138. For example, the end 136 is shown in a curled or coiled position. A sleeve 140 extends over a distal portion 142 of the bladder end 136. The sleeve 140 covers a luminal groove 144, which is cut into a central lumen 147, as shown in FIGS. 5B and 5C. Urine drains through the central lumen 147 (which extends inside the stent body 132, for example, at the bladder end 136). The sleeve 140 is such that it extends beyond the luminal groove 144, both proximally and distally at the end 136.

The sleeve 140 is made of, a material having a softer durometer than the materials for the stent 130. The sleeve 140 is frictionally fit over the distal portion 142 of the bladder end 136, of the stent 130. Additionally, the sleeve 140 is such that the urine force is greater than the radial tensile force of the sleeve 140, allowing urine pressure in the lumen 147 of the stent 130 to cause the sleeve 140 to expand, for example, outward from the stent body 132. This expansion outward by the sleeve 140, allows urine to leave the stent 130 at the bladder end 136, by flowing between the stent 130 and the sleeve 140 (e.g., under the sleeve 140), and entering the bladder. This arrangement of the sleeve 140 on the stent 130, coupled with the materials from which the sleeve 140 is made, serves to prevent vesico-ureteral reflux. Materials for the sleeve 140 include soft silicones and other silicone rubbers, for example, Elastosil® LR 3003/30 from Wacker Chemie AG of Germany, and Silbione® LSR 4330/ 4340, from Bluestar Silicones of France.

The portion 150 of the sleeve facing and covering the luminal groove 144 is, for example, preshaped in a concave (inward) manner, to ease the prevention of reflux, as shown in FIGS. 5A-5C. The portion 150 is, for example, preshaped cylindrically (convex or outward), also to ease the prevention of reflux, as shown in FIGS. 6A-6C.

The stent 130, such as the right 130R and left 130L, stents, are made of materials such as polymeric materials, including thermoplastic materials, such as polyurethanes or co-polymers, and thermoset elastomers, such as silicone and hydrogels, or tightly coiled polymeric or metal wires. The walls of the stent 130 (130R, 130L) may be reinforced with embedded coiled, or longitudinal wires or braids.

Figure 7:
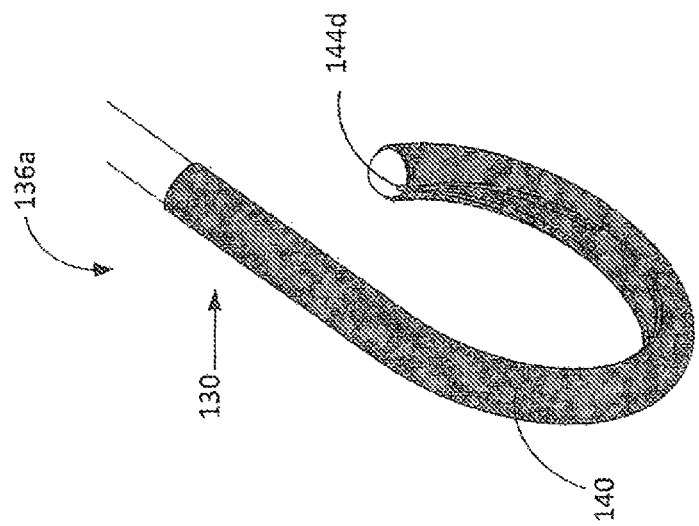
FIG. 7 is a perspective view of the bladder end of the stent and lumenal groove of FIGS. 5A-5C and 6A-6C.

FIG. 7 shows the bladder end 136 of the stent with the sleeve 130, as detailed above, and shown in FIGS. 3A-3C, 4, 5A-5C and 6A-6C.

Figure 8:
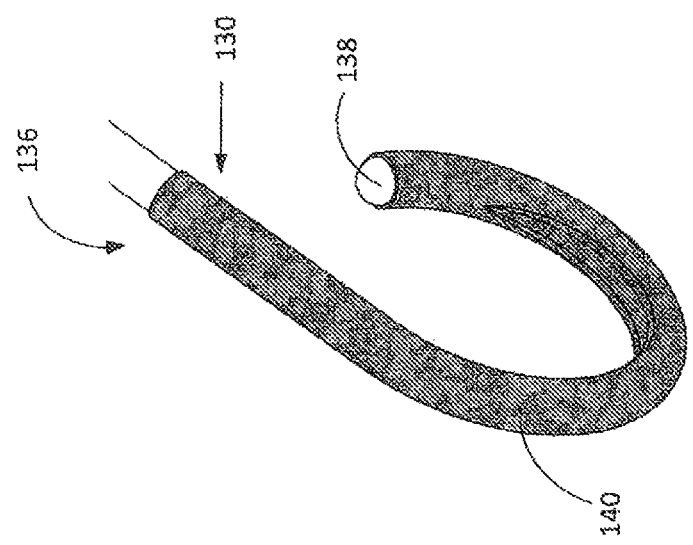
FIG. 8 is, a perspective view of an alternative embodiment of the bladder end of the stent and lumenal groove of FIG. 7.
Figure 9C:
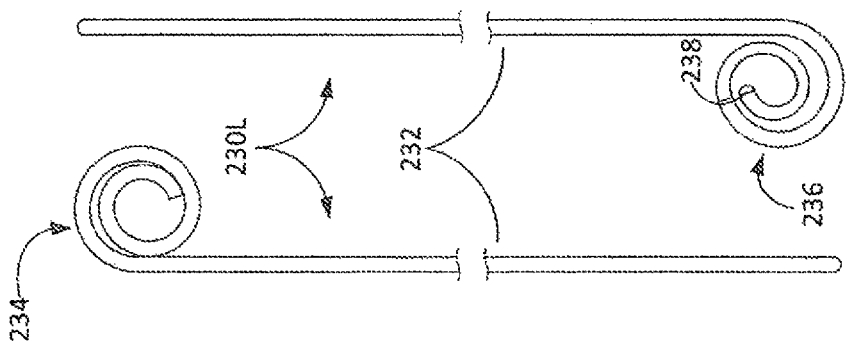
FIG. 9C are front and side views of left side stents in accordance with the embodiment of FIG. 9A.
Figure 9B:
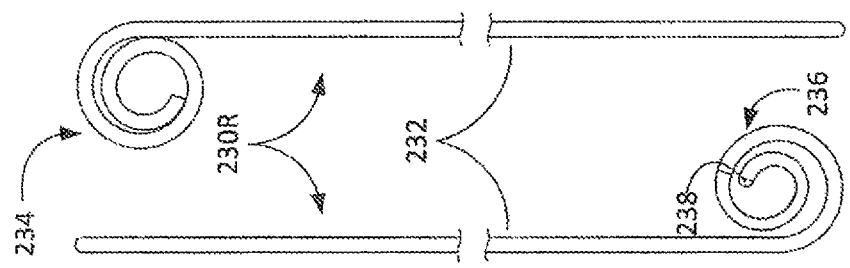
FIG. 9B are front and side views of right side stents in accordance with the embodiment of FIG. 9A.
Figure 9A:
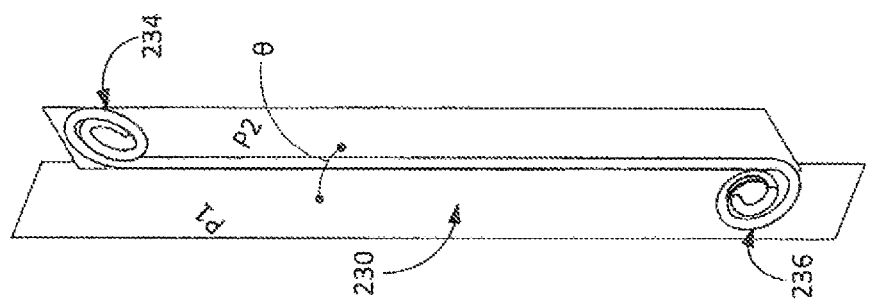
FIG. 9A is a perspective view of a Pigtail stent in accordance with an embodiment of the present invention.

FIG. 8 shows an alternative bladder end 136a of the stent 130. In this alternative end 136a, the luminal or intraluminal groove 144 extends to the tip 138, and the sleeve 140 terminates at the distal end 144d of the luminal groove 144. The sleeve 140 is made of a flexible and radially elastic material softer (e.g., in durometer) than the materials of the remainder of the body 132 of the stent 130. When the pressure in the bladder increases, the sleeve 140 collapses into the luminal groove 144 to prevent urine reflux from the bladder through the stent 130 toward the kidney. Urine at sufficient pressures can pass out from the stent 130, between the stent 130 and the sleeve 140, the pressure of the urine pushing or expanding a part of the edge 140e of the sleeve 140 to elevate it and allow passage of urine.

The softness and elasticity of the sleeve 140 allows for a guide wire (not shown) to pass through the bladder end 130a beneath the sleeve 140 and the tip 138. The function of the guide wire is detailed further below.

FIGS. 9A-9C, 10A-10C, 11A-11C, 12A-12B, 13A and 13B, show a pigtail stent 230 in accordance with embodiments of the present invention. The components and elements of the pigtail stent 230, are similar to those of the stent 130, these components and elements having the same numbering in the "200s" (the numbering of the same or similar elements of the stents 130, 130R, 130L, increased by "100"), and in accordance with those components and elements for the stents 130, 130R, 130L, as described above.

In the pigtail stent 230, 230R, 230L, the kidney end 234 and the bladder end 236 are curled or coiled, for example, with each of the curls or coils at the ends 134, 136 of the pigtail stents 230, 230R, 230L, repeating itself one or more times. The pigtail stents 230, 230R, 230L of FIGS. 9A-9C have components corresponding to those of the Double-J stents 130, 130R, 130L, as shown in FIGS. 3A-3C and described above, except where specifically indicated.

FIGS. 10A-10C detail the bladder end 236 for the stent 230. The bladder end 236 is made of multiple portions of materials of different hardnesses, or different durometers. For example, the bladder end 236 is formed of for example, three portions, moving distally, a first or proximal most portion 237a, a second or intermediate portion 237b, and a third or distal most portion 237c. The intraluminal groove 244, similar to, and in accordance with the intraluminal groove 144, as described above, for example, is positioned in the third or distal portion 237c of the bladder end 236 of the stent 230.

The first 237a and the third 237c portions can be made of the same relatively harder material or same durometers as the rest of the stent 230. The intermediate portion 237b is made of a hardness or durometer lower than the durometer of the proximal 237a and distal 237b portions. These differences in hardness produce an intermediate portion 237b, which is softer and more flexible than the two relatively harder portions 237a, 237c. This arrangement allows for easier curling, or coiling and at least partially uncurling or at least partially uncoiling of the bladder end 236. Alternately, the bladder end 236 may be entirely made of a single-hardness material but soft enough to curl or coil and at least partially uncurl or uncoil during respiration. The same hardness differences can be applicable also to the Double-J stents 130, 130R, 130L, detailed above.

Figure 11C:
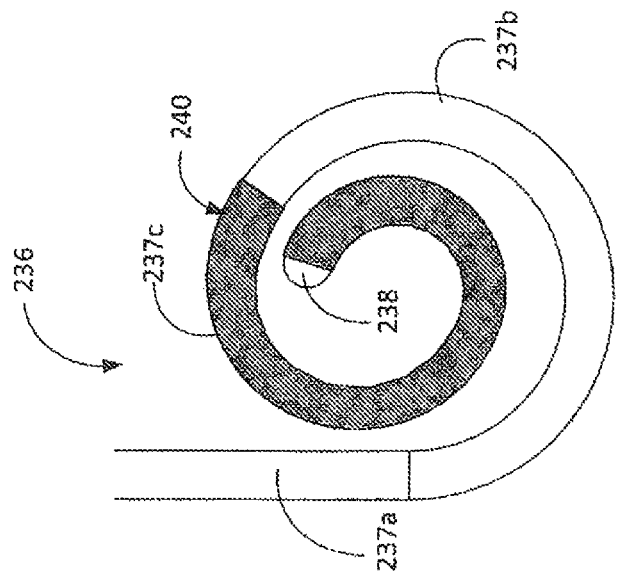
FIG. 11C is a side view of the bladder end of the Pigtail Stent of FIG. 9A, with the sleeve attached.
Figure 11B:
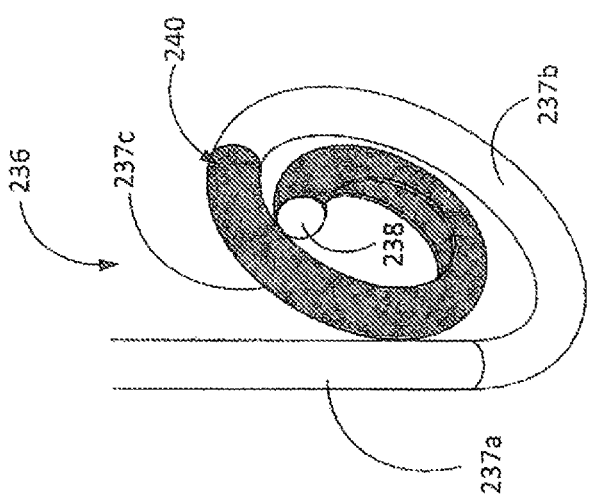
FIG. 11B is a perspective view of the bladder end of the Pigtail Stent of FIG. 9A, with the sleeve attached.
Figure 11A:
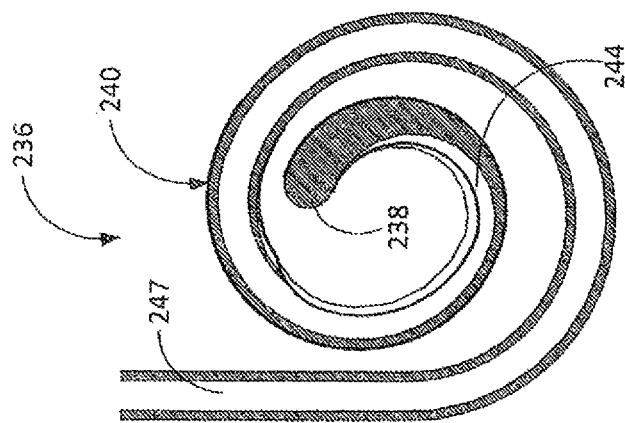
FIG. 11A is a longitudinal-sectional view of the bladder end of the Pigtail Stent of FIG. 9A, with the sleeve attached.

FIGS. 11A-11C show the sleeve 240 that covers the distal portion 237c of the bladder end 236, shown also in FIGS. 10A-10C. The sleeve 240 is in accordance with the sleeve 140 as detailed above. The sleeve 240 extends from a point proximal to the tip 238 and extends proximally along the end 236, to extend beyond the ends of the luminal groove 244, covering the luminal groove 244. The sleeve 240 may extend over the intermediate portion 237b and proximal portion 237a of the end 236.

Figure 2A:
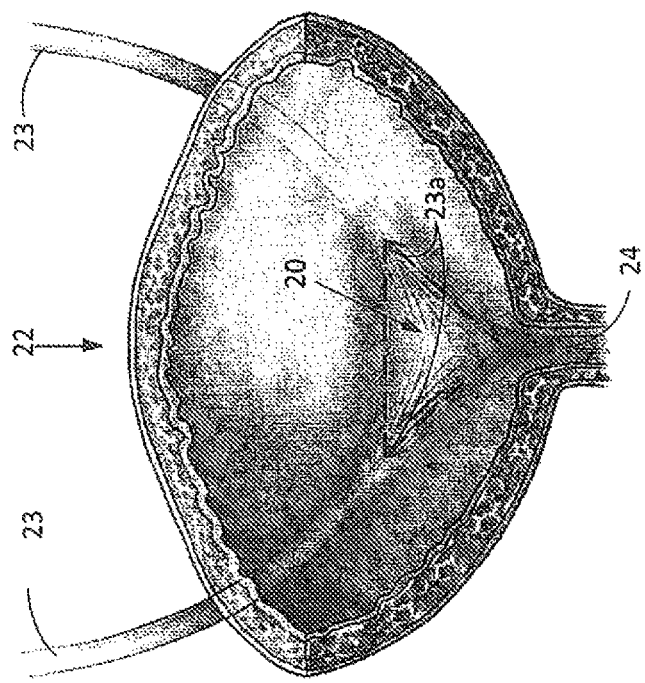
FIG. 2A is a diagram of the bladder, showing the trigone of the bladder.
Figure 12A:
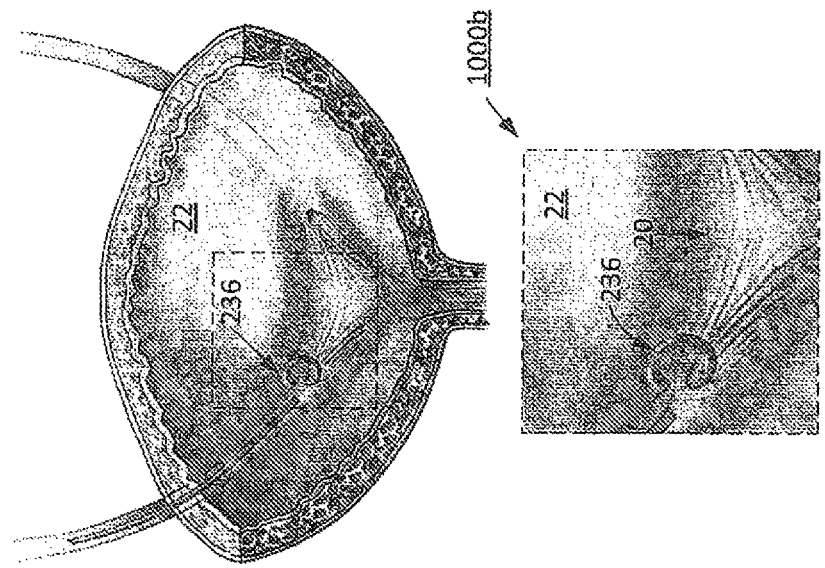
FIG. 12A is a diagram of the bladder showing the Pigtail stent of FIG. 9A deployed in the bladder and the bladder end being coiled to remain substantially out of frictional contact with the trigone of the bladder during inspiration.
Figure 12B:
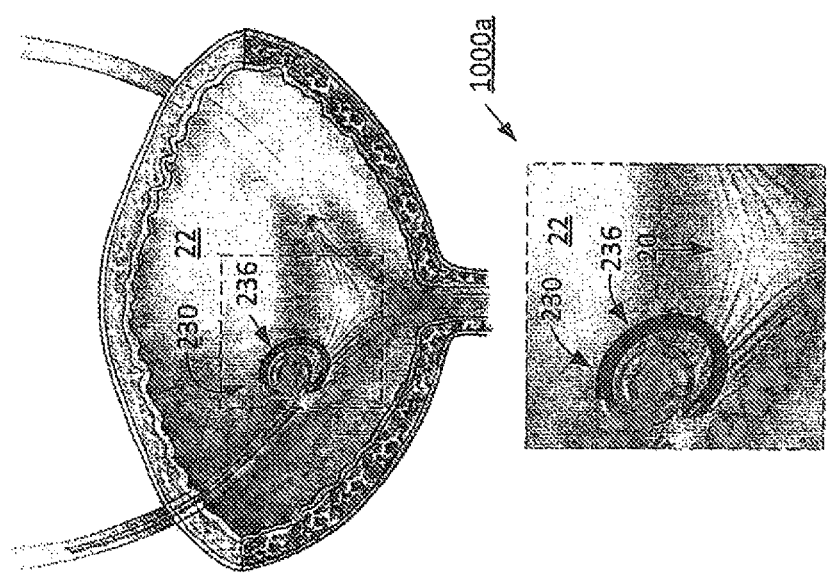
FIG. 12B is a diagram of the bladder showing the Pigtail stent of FIG. 9A deployed in the bladder and the bladder end being uncoiled and substantially out of frictional contact with the trigone of the bladder during expiration.

For example, and turning also to FIGS. 12A and 12B, including the respective detail boxes 1000a and 1000b, which show the pigtail stent 230R, representative of pigtail stents 230, 230L disclosed herein inside of the bladder 22. The stent 230R of FIG. 12A is in the curled or coiled position at the bladder end 236, during inspiration (FIG. 2A), where the kidney is at the lowest point in the body during respiration (the "short" distance between the kidney and the bladder).

In FIG. 12B, the stent 230R at the bladder end 236 is in the partially uncurled or partially uncoiled position, as shown during expiration, when the kidney is at its highest point in the body during respiration (the "long" distance between the kidney and the bladder). For example, in humans, the difference between kidney positions can be up to 4 cm. For example, by making the stents 230, 230R, 230L at lengths according to the "short" distance between the kidney and the bladder, coupled with the stents 230, 230R, 230L to change their bladder-end geometry between the curled or coiled and at least partially uncurled or uncoiled positions, the stents 230, 230R, 230L can compensate for the occurring kidney to bladder distance changes during respiration. The bladder end 136 of the Double-J stents 130 detailed above perform in a similar manner when deployed in the bladder.

Figure 13C:
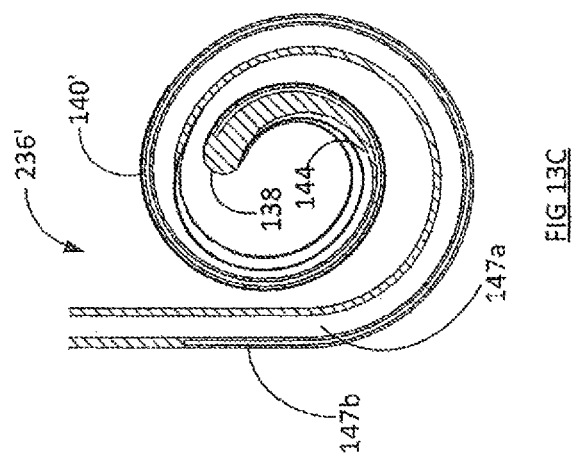
FIG. 13C is a longitudinal sectional view of an alternative Pigtail stent of FIG. 13A in accordance with an embodiment of the present invention.
Figure 13B:
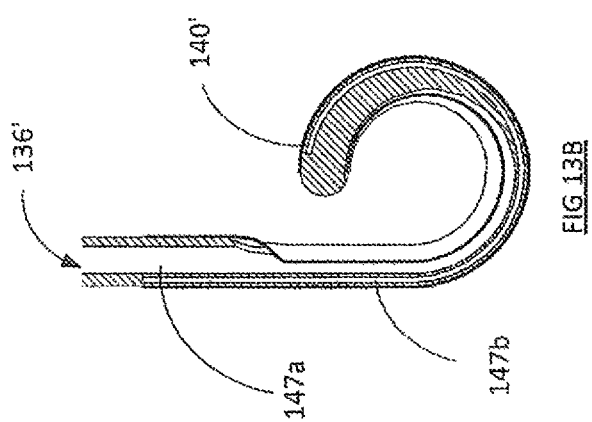
FIG. 13B is a cross sectional view of an alternative Double-J stent of FIG. 13A in accordance with an embodiment of the present invention.
Figure 13A:
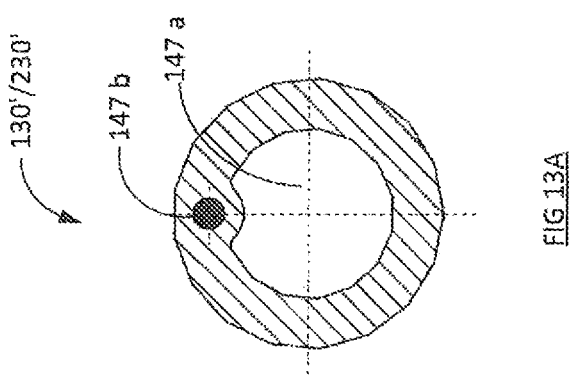
FIG. 13A is a longitudinal sectional view of a portion of a Double-J stent and a Pigtail stent in accordance with alternative embodiments of the present invention.

Attention is now directed to FIGS. 13A-13C. These figures show an alternative Double-J stent 130'/pigtail stent 230' with an alternative bladder end 136'/236'. These alternative stents 130'/230' are in accordance with the, respective Double-J 130, 130R, 130L and pigtail stents 230, 230R, 230L detailed above, except where indicated.

FIG. 13A shows the stents 130'/230' along their respective bodies 132/232 as including a central lumen 147a/247a, 147b/247b and a longitudinal housing lumen 147b/247b. The larger lumen is a central or primary lumen 147a/247a, for urine drainage, while the smaller or secondary lumen

147b/247b is a housing for a pre-shaped wire to help the softer part of the bladder end 236' to recurl or recoil at inspiration. The reinforcing wire may be preshaped, made of polymers, stainless steel or Nitinol, with the preshaping causing the ends 234, 236' to curl and at least partially uncurl (or coil or at least partially uncoil) as disclosed herein for stents 130 and 230, for example. The central lumen 147a/247a, for example, includes an intraluminal groove 144/244, as detailed above, which is covered by a sleeve 140/240, as detailed above. The sleeve 140/240, for example, extends along the bladder end 136'/236' beyond the ends of the intraluminal groove 144/244.

FIG. 13B shows the bladder end 136' of the Double-J stent 130', in a curled or coiled position. FIG. 13C shows the bladder end 236' of the pigtail stent 230' in a curled or coiled position.

While the bladder ends 136'/236' of the double-J stent 130', and the pigtail stent 230', are formed of a single material, the bladder ends 136'/236' may also be made of three portions, like that of the stent 230 and bladder end 236, as detailed above, and shown in FIGS. 10A-10C and 11A-11C.

FIGS. 14A and 14B show a measuring device 1100 for measuring the length of the ureter. The device 1100 includes a ureter length measuring tube 1102, mounted on a handle 1104, with a pulling wire 1106 attached at its distal end 1109. A slider 1110, moveably mounted in the handle 1104, pulls the wire 1106 (extending in the measuring tube 1102), which opens the Malecot-like flanges 1112 (FIG. 14B) at the slit 1107 at the distal end 1109 of the measuring device 1100, allowing the Malecot-like flanges 1112 to open and anchor the tip of the measuring tube 1102 at the kidney pelvis. The lumen 1114 of the measuring tube 1102 and the handle 1104 can accommodate a guide wire (not shown).

Alternatively, the measuring tube 1104 may have multiple, for example, dual, separate lumens, one for the pulling wire 1106 and the second for the guidewire. The ureter length can now be endoscopically seen on the measuring tube 1102, extending outward from the ureter orifice. The device 1100 is deployed and removed in the position of FIG. 14A, while the ureter length is measured with the device 1100 in the position of open Malecot-like flanges shown in FIG. 14B. This measured length allows for selection of a stent with the proper length. Instead of the flanges, an inflatable balloon, which is inflated through a separate lumen, can be used for fixing the device and measuring the ureter length.

FIG. 15 shows the stent 130 (representative of all stents 130, 130', 230, 230' disclosed herein) upon its deployment into the body. A guide wire 1210 passing through the stent lumen 147 and coming out from its bladder end groove, is inserted into the pusher member 1212 through a side opening 1214 in the pusher member 1212, into its central lumen 1215. Once the guide wire 1210 is inserted completely into the pusher member 1212 and the proximal tip 130p of the stent 130 comes into contact with the distal tip 1212d of the pusher member 1212, the pusher member 1212 is moved forward. This forward movement pushes the stent 130 (which is over the guide wire 1210) into position, from the bladder to the kidney, through the ureter.

While the stents 130, 130', 230, 230' of the present invention have been shown and described above for urinary applications, this is exemplary only. These stents 130, 130', 230, 230' of the present invention as disclosed herein, are easily adapted for use in uretero-enteric anastomoses, biliary and pancreatic applications, as well as for other instances where reflux should be inhibited.

As used herein, the singular form "a", "an", and "the" include plural references unless the context clearly dictates otherwise.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A stent comprising:
    a body including oppositely disposed first and second curled ends, the first curled end extending along a first plane and the second curled end extending along a second plane, the first and second planes at different orientations with respect to each other;
    wherein the body is tubular and includes:
    an outer surface;
    an interior lumen;
    the second curled end of the body having a closed tip and including an elongated groove extending longitudinally to and through the body into the interior lumen, from the outer surface of the body; and,
    a sleeve extending at least partially along the elongated groove over the body, said sleeve comprising a material having a lower durometer than the body of the stent;
    wherein said sleeve is configured with respect to said elongated groove so that when pressure within said second curled end is sufficient said sleeve is forced to expand allowing liquid egress between said body and said sleeve from said elongated groove, and when pressure inside a bladder increases said sleeve collapses into said elongated groove preventing liquid from migrating from said second curled end back towards said first curled end.

2. The stent of claim 1, wherein the different orientations of the first and second planes with respect to each other include angles ranging from approximately 60 degrees to approximately 120 degrees.

3. The stent of claim 1, wherein the different orientations of the first and second planes with respect to each other include perpendicular orientations.

4. The stent of claim 1, wherein the first curled end and the second curled end are moveable between a curled position and a partially uncurled position to accommodate respiration of a user.

5. The stent of claim 1, wherein the second curled end is configured for placement at least partially in said bladder.

6. The stent of claim 1, wherein the sleeve extends beyond ends of the elongated groove.

7. A stent comprising:
a body including:
an inner lumen;
oppositely disposed first and second curled ends, and, an outer surface;
the second curled end having a closed tip and including an elongated groove extending longitudinally to and through the body into the inner lumen from the outer surface of the body; and,
a sleeve extending at least partially along the elongated groove over the body, said sleeve comprising a material having a lower durometer than the body of the stent;
wherein said sleeve is configured with respect to said elongated groove so that when pressure within said second curled end is sufficient said sleeve is forced to expand allowing liquid egress between said body and said sleeve from said elongated groove, and when pressure inside a bladder increases said sleeve collapses into said elongated groove preventing liquid from migrating from said second curled end back towards said first curled end.

8. The stent of claim 7, wherein the sleeve extends beyond ends of the elongated groove.

9. The stent of claim 7, wherein the first curled end extends along a first plane and the second curled end extends along a second plane, the first and second planes at different orientations with respect to each other.

10. The stent of claim 9, wherein the different orientations of the first and second planes with respect to each other include angles ranging from approximately 60 degrees to approximately 120 degrees.

11. The stent of claim 9, wherein the different orientations of the first and second planes with respect to each other include perpendicular orientations.

12. The stent of claim 7, wherein the first curled end and the second curled end are moveable between a curled position and a partially uncurled position to accommodate respiration of a user.

13. The stent of claim 7, wherein the second curled end is configured for placement at least partially in said bladder.

14. The stent of claim 7, wherein the body is tubular.

15. A drainage device comprising:
a body including an inner lumen, the body including oppositely disposed first and second curled ends, the first curled end extending along a first plane and the second curled end extending along a second plane, the first and second planes at different orientations with respect to each other;
wherein the body is tubular and includes:
an outer surface;
the second curled end of the body having a closed tip and including an elongated groove extending longitudinally to and through the body into the inner lumen, from the outer surface of the body; and,
a sleeve extending at least partially along the elongated groove over the body, and wherein said sleeve comprises a material having a lower durometer than the body of the stent;
wherein said sleeve is configured with respect to said elongated groove so that when pressure within said second curled end is sufficient said sleeve is forced to expand allowing liquid egress between said body and said sleeve from said elongated groove, and when pressure inside a bladder increases said sleeve collapses into said elongated groove preventing liquid from migrating from said second curled end back towards said first curled end.

16. The device of claim 15, wherein the different orientations of the first and second planes with respect to each other include angles ranging from approximately 60 degrees to approximately 120 degrees.

17. The device of claim 15, wherein the different orientations of the first and second planes with respect to each other include perpendicular orientations.

18. The device of claim 15, wherein the body defines a stent.

19. The device of claim 18, wherein the stent is selected from the group of urinary stents, biliary stents, and pancreatic stents.

20. The device of claim 18, wherein the device is a urinary stent and the first curled end and the second curled end are moveable between a curled position and a partially uncurled position to accommodate respiration of a user.

21. The device of claim 20, wherein the second curled end is configured for placement at least partially in said bladder.

22. A drainage device comprising:
a tubular body including:
an inner lumen;
oppositely disposed first and second curled ends, an outer surface;
the second curled end having a closed tip and including an elongated groove extending longitudinally to and through the tubular body into the inner lumen from the outer surface of the tubular body; and,
a sleeve extending at least partially along the elongated groove over the tubular body;
wherein said sleeve is configured with respect to said elongated groove so that when pressure within said second curled end is sufficient said sleeve is forced to expand allowing liquid egress between said tubular body and said sleeve from said elongated groove, and when pressure inside a bladder increases said sleeve collapses into said elongated groove preventing liquid from migrating from said second curled end back towards said first curled end.

23. The device of claim 22, wherein the sleeve extends beyond ends of the elongated groove.

24. The device of claim 22, wherein the sleeve is of a material having a lower durometer than the tubular body.

25. The device of claim 22, wherein the first curled end extends along a first plane and the second curled end extends along a second plane, the first and second planes at different orientations with respect to each other.

26. The device of claim 25, wherein the different orientations of the first and second planes with respect to each other include angles ranging from approximately 60 degrees to approximately 120 degrees.

27. The device of claim 25, wherein the different orientations of the first and second planes with respect to each other include perpendicular orientations.

28. The device of claim 22, wherein the tubular body defines a stent.

29. The device of claim 28, wherein the stent is selected from the group of urinary stents, biliary stents, and pancreatic stents.

30. The device of claim 28, wherein the device is a urinary stent and the first curled end and the second curled end are moveable between a curled position and a partially uncurled position to accommodate respiration of a user.

31. The device of claim 30, wherein the second curled end is configured for placement at least partially in said bladder.

32. A method for facilitating urine drainage comprising:
providing a stent comprising a body including oppositely disposed first and second curled ends, the first curled end extending along a first plane and the second curled end extending along a second plane, the first and second planes at different orientations with respect to each other;
wherein the body is tubular and includes:
an outer surface;
an interior lumen;
the second curled end of the body having a closed tip and including an elongated groove extending longitudinally to and through the body into the interior lumen, from the outer surface of the body; and,
a sleeve extending at least partially along the elongated groove over the body, and wherein the said sleeve is of a material having a lower durometer than the body of the stent;
deploying the stent via a ureter, wherein the first curled end extends at least to a kidney and the second curled end extends at least into a bladder, such that the first curled end along the first plane is disposed at an angle from the second curled end along the second plane;
wherein said sleeve is configured with respect to said elongated groove so that when pressure within said second curled end is sufficient said sleeve is forced to expand allowing liquid egress between said body and said sleeve from said elongated groove, and when pressure inside said bladder increases said sleeve collapses into said elongated groove preventing liquid from migrating from said second curled end back towards said first curled end.

33. The method of claim 32, wherein the angle is approximately 30 to 150 degrees.

34. The method of claim 32, wherein the angle is approximately 90 degrees.

35. The method of claim 32, wherein the step of providing the stent includes measuring a length of the ureter from the kidney to the bladder, and selecting the stent according to the measured length of the ureter.

36. The method of claim 32, wherein the step of deploying includes moving the stent along a guide wire.

* * * * *